United States Patent [19]
Godolphin et al.

[11] Patent Number: 5,413,246
[45] Date of Patent: * May 9, 1995

[54] APPARATUS AND METHOD FOR ALIQUOTTING PHASES OF BLOOD

[75] Inventors: William J. Godolphin, Vancouver; Winona C. Specht; David P. Pires, both of North Vancouver; Geoffrey T. Killam, Burnaby, all of Canada

[73] Assignee: Automed Corporation, Richmond, Canada

[*] Notice: The portion of the term of this patent subsequent to May 18, 2010 has been disclaimed.

[21] Appl. No.: 57,306

[22] Filed: May 5, 1993

Related U.S. Application Data

[63] Continuation of Ser. No. 693,653, Apr. 30, 1991, Pat. No. 5,211,310.

[51] Int. Cl.⁶ .............................................. B65G 59/00
[52] U.S. Cl. ........................................ 222/1; 222/61; 222/82; 222/394; 422/67; 422/100
[58] Field of Search ...................... 222/1, 83, 83.5, 61, 222/64, 167, 394, 399, 400.7, 400.8, 401, 82; 210/104, 514, 520; 422/64, 67, 100, 102; 604/411

[56] References Cited

U.S. PATENT DOCUMENTS

| | | |
|---|---|---|
| 2,460,641 | 8/1945 | Kleiner . |
| 3,288,318 | 11/1966 | Corbin . |
| 3,341,073 | 9/1967 | Arps et al. . |
| 3,438,549 | 4/1969 | Ritz . |
| 3,456,647 | 7/1969 | Wada . |
| 3,596,673 | 8/1971 | Laucournet . |
| 3,782,548 | 1/1974 | Bowen . |
| 3,849,072 | 11/1974 | Ayres . |
| 3,885,607 | 5/1975 | Peltier . |
| 3,932,277 | 1/1976 | McDermott . |
| 3,941,171 | 3/1976 | Ogle . |
| 4,000,829 | 1/1977 | Johnson, Jr. et al. . |

(List cntinue on next page.)

FOREIGN PATENT DOCUMENTS

| | | |
|---|---|---|
| 0263753 | 4/1988 | European Pat. Off. . |
| 0285076 | 10/1988 | European Pat. Off. . |
| 0341586 | 11/1989 | European Pat. Off. . |
| 0341587 | 11/1989 | European Pat. Off. . |
| 0348116 | 12/1989 | European Pat. Off. . |
| 0409650 | 1/1993 | European Pat. Off. . |
| 2487802 | 2/1982 | France . |
| 2637376 | 4/1990 | France . |
| WO87/05208 | 9/1987 | WIPO . |

OTHER PUBLICATIONS

Tecan Robotic Sample Processor Series 5000, 5 pages.
U.S. Pat. No. 4,169,060, *Official Gazette* notice & abstract, 2 pgs, Sep. 25, 1979.
U.S. Pat. No. 4,847,205, *Official Gazette*, 2 pgs, Jul. 11, 1989.
Baxter Healthcare; *New Software MC 2.0* Brochure, 2 pgs, Jul. 1990.
Serumax Medical Robotics, 3 pgs.

(List continued on next page.)

*Primary Examiner*—Gregory L. Huson
*Attorney, Agent, or Firm*—Klarquist Sparkman Campbell Leigh & Whinston

[57] ABSTRACT

A disposable apparatus to dispense an amount of liquid from a closed container such as a stoppered blood collection tube. The apparatus comprises a stopper piercing means to access the interior of a closed blood collection tube; a gas passage means to allow a metered amount of gas to be forced into the blood collection tube; and, a liquid passage means to allow fluid to be dispensed from the tube in proportion to the amount of gas forced into the tube. Also disclosed is a machine which uses a disposable apparatus to dispense liquid from a sequence of closed blood collection tubes in an automated manner. Liquid contained within a blood collection tube is dispensed from the tube by a control means according to signals indicative of the amount of liquid within the tube and the amount of liquid that is desired to be dispensed. A manually operated machine that uses the disposable apparatus to dispense a sample of liquid from a closed blood collection tube is also described.

13 Claims, 8 Drawing Sheets

U.S. PATENT DOCUMENTS

| | | |
|---|---|---|
| 4,021,352 | 5/1977 | Sarsedt . |
| 4,046,699 | 9/1977 | Zine, Jr. . |
| 4,131,217 | 12/1978 | Sandegren . |
| 4,192,438 | 3/1980 | Foster et al. . |
| 4,274,453 | 6/1981 | Lee . |
| 4,295,065 | 5/1990 | Golias . |
| 4,326,959 | 4/1982 | Ferrara . |
| 4,347,874 | 9/1982 | Sullivan et al. . |
| 4,373,559 | 2/1983 | Mowles et al. . |
| 4,478,095 | 10/1984 | Bradley et al. . |
| 4,522,713 | 6/1985 | Nussbaumer . |
| 4,532,969 | 8/1985 | Kwaan . |
| 4,535,918 | 8/1985 | Heiligman et al. . |
| 4,583,664 | 4/1986 | Bayat . |
| 4,630,753 | 12/1986 | Anscherlik . |
| 4,811,866 | 3/1989 | Golias . |
| 4,815,325 | 3/1989 | Averette . |
| 4,861,553 | 8/1989 | Mawhirt et al. . |
| 4,959,053 | 9/1990 | Jang ................................ 604/127 |
| 4,968,485 | 11/1990 | Morita ................................ 422/100 |
| 4,976,925 | 12/1990 | Porcher et al. . |
| 4,993,601 | 2/1991 | Nakayama et al. . |
| 5,019,243 | 5/1991 | McEwen . |
| 5,030,341 | 7/1991 | McEwen . |
| 5,041,106 | 8/1991 | Noji et al. ........................ 604/411 |
| 5,049,359 | 9/1991 | Azuma . |
| 5,065,907 | 11/1991 | Allen . |
| 5,074,437 | 12/1991 | D'Andrade et al. ............... 222/79 |
| 5,078,970 | 1/1992 | Teodorescu et al. ............. 422/100 |
| 5,163,582 | 11/1992 | Godolphin et al. ......... 222/400.7 X |
| 5,211,310 | 5/1993 | Godolphin et al. ................... 222/1 |

OTHER PUBLICATIONS

*Idea Caps Risks in Lab*, 1 p., The London Sunday Times, Jan. 24, 1988.

*An Automated Device for Aseptically Aspiring Serum From Blood Collection Tubes*, 7 pages, Jun. 1986; IEEE Translation on Biomedical Engineering.

Development of a Simple Device for Processing Whole-Blood Samples into Measured Aliquots of Plasma, 6 pages, 1986; Clinical Chemistry, vol. 32, No. 9.

International Search Report for application No. PCT/CA92/00181 dated Aug. 5, 1992.

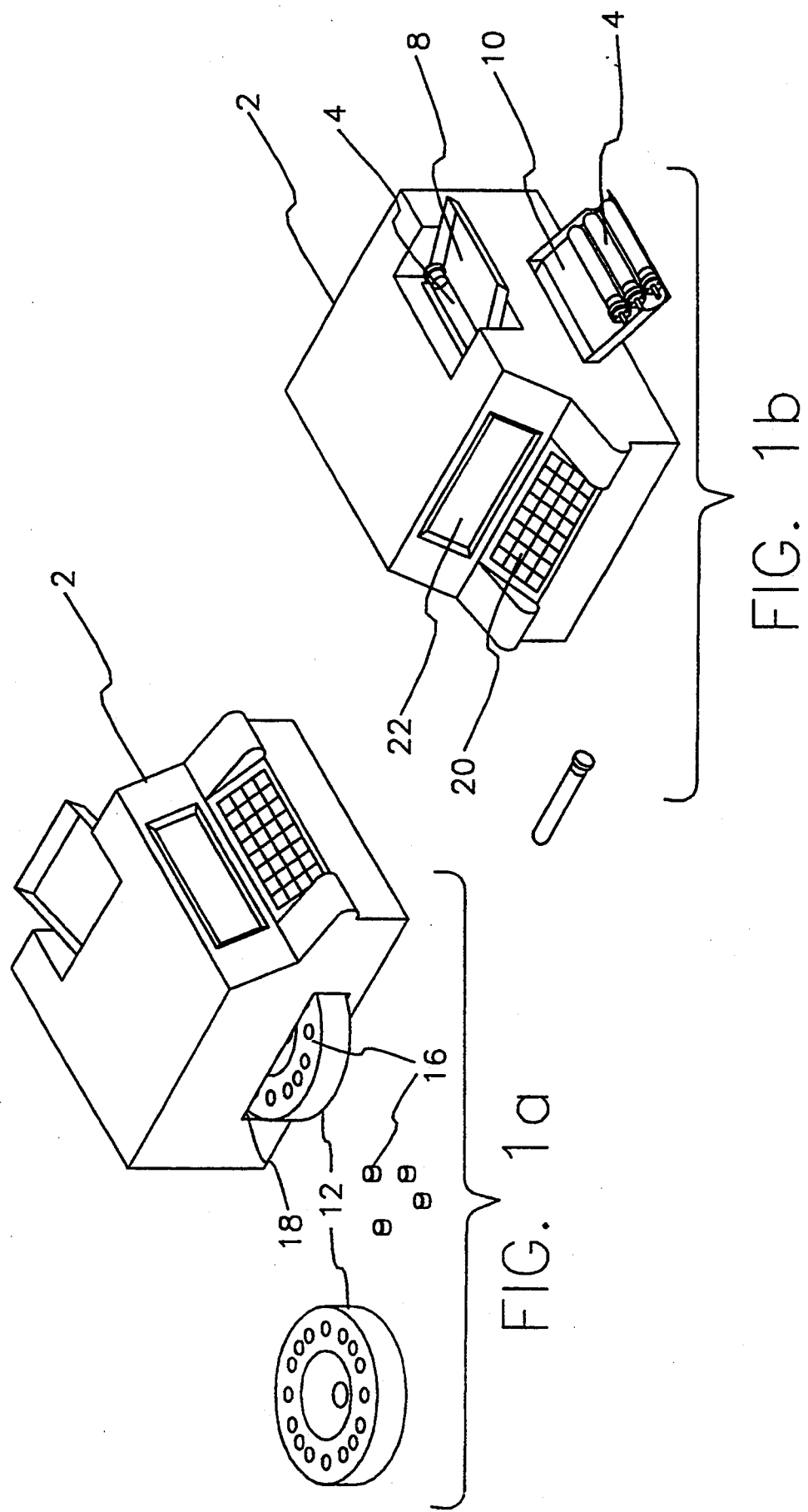

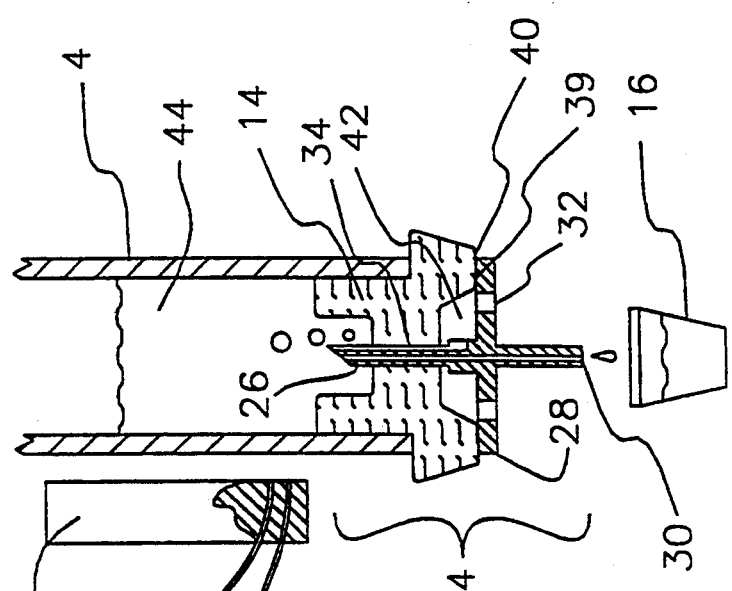
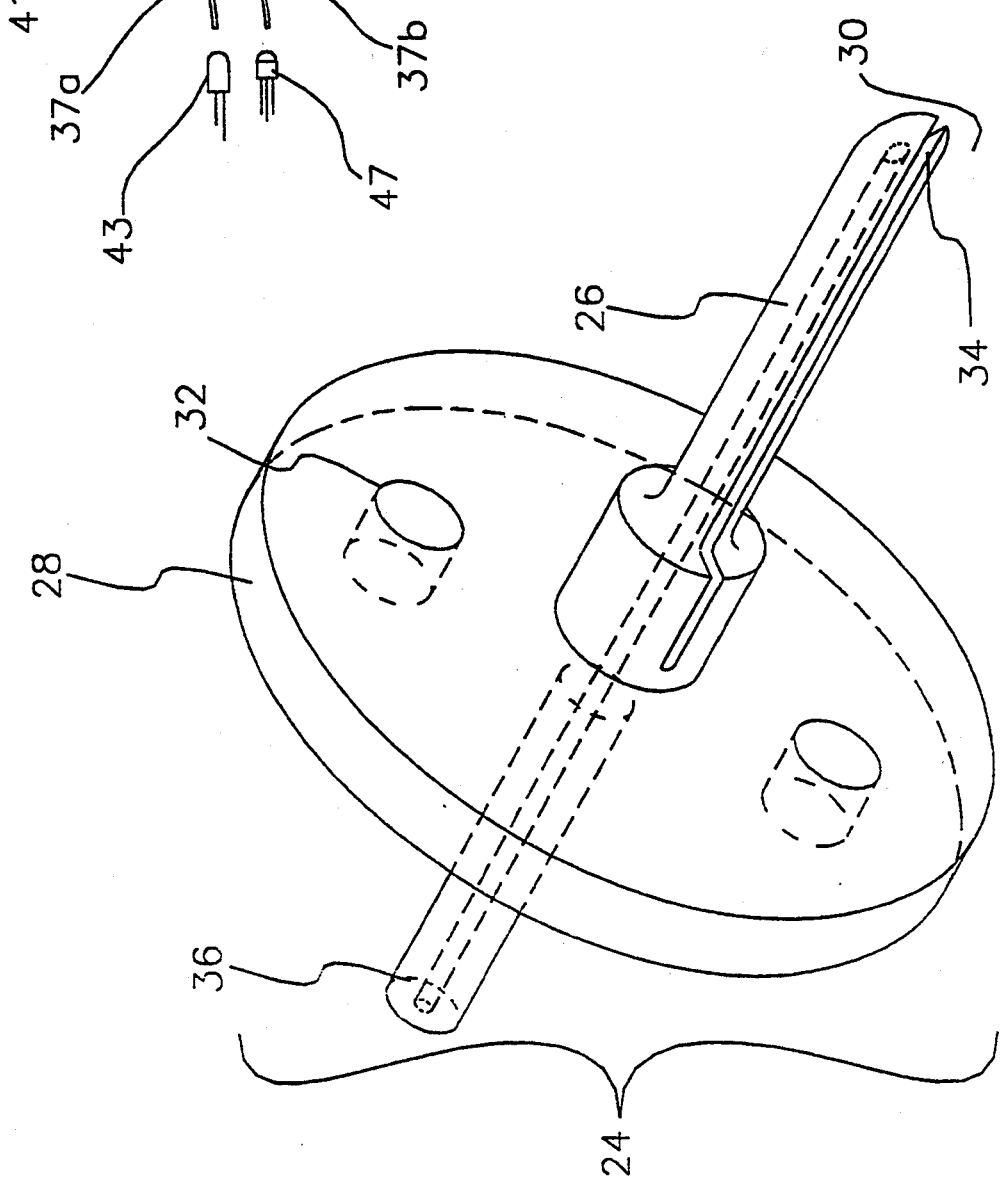
FIG 2b
FIG 2a

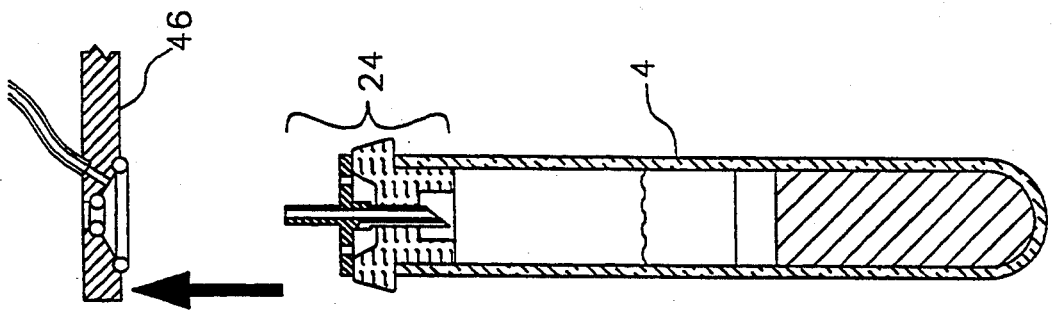
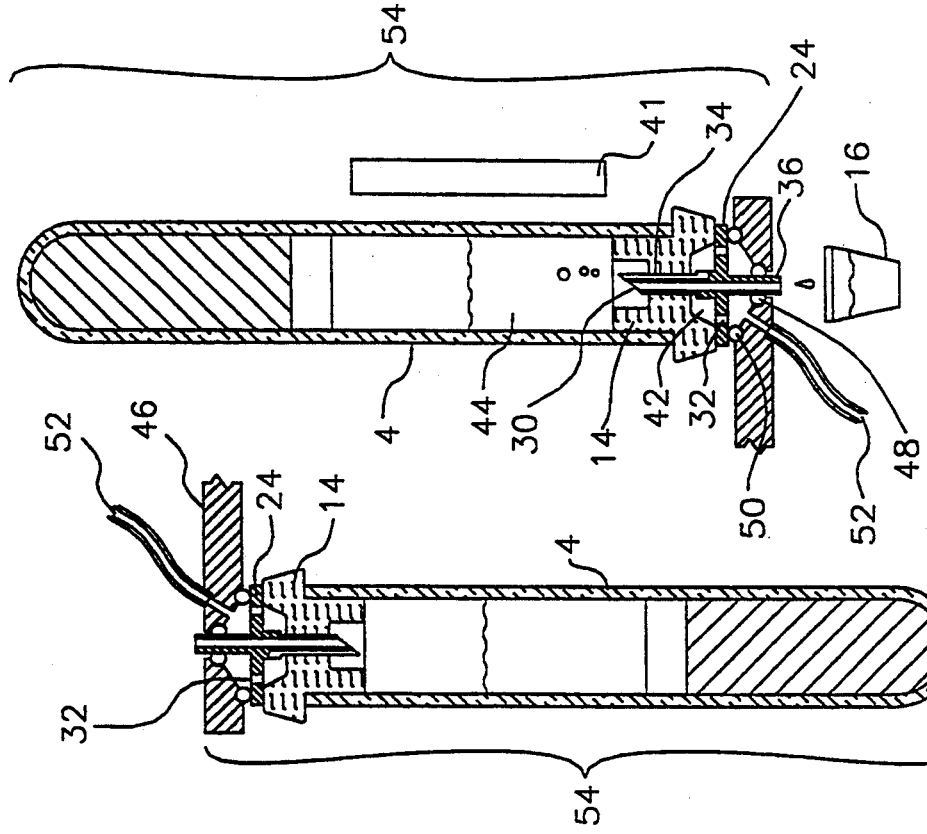
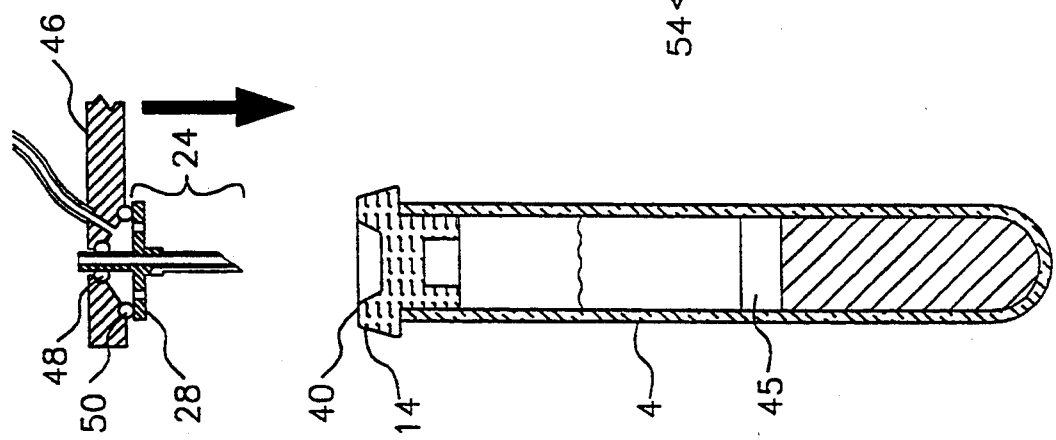
FIG 3a  FIG 3b  FIG 3c  FIG 3d

APPARATUS AND METHOD FOR ALIQUOTTING PHASES OF BLOOD

This application is a continuation of application Ser. No. 07/693,653, filed Apr. 30, 1991 now U.S. Pat. No. 5,211,310, issued May 18, 1993.

FIELD OF THE INVENTION

The present invention refers to a method and apparatus for dispensing a sample of fluid from a closed chamber and pertains to displacing fluid contained within a chamber with a volume of gas thereby forcing a quantity of fluid from the chamber. In particular the invention pertains to a method for dispensing fluid from a closed chamber and an apparatus for causing fluid contained within the chamber to be dispensed.

BACKGROUND OF INVENTION

Major sources for concern in clinical laboratories are the safety, costs and efficiency of the normal procedures for preparation of specimens, such as blood, prior to analysis. Blood specimens for clinical analyses are commonly collected in evacuated blood collection tubes. Serum or plasma may be isolated from the cellular material by centrifugation and transferred or aliquotted to one or more specialized sample vessels. These sample vessels are used to introduce a portion of the specimen to chemical analyzers.

The hazards, labour and errors associated with these preanalytic accessioning procedures could be reduced by automation.

Several aspects of the aliquotting procedure must receive critical attention:

(1) The process exposes laboratory personnel to the hazard of direct contact with a biological fluid which may contain infectious agents such as hepatitis or acquired immune deficiency syndrome (AIDS). Technology which reduces or prevents the direct contact by permitting automated removal of serum or plasma from the blood collection tube, without need to remove the stopper would considerably reduce the hazard.

(2) Manual handling of glass apparati (syringes, blood collection tubes, pipettes) exposes technologists to hazards of spillage and breakage and may result in the loss of a specimen of high clinical value. Ideally a sample of serum or plasma should be transferred directly from the collection tube to the recipient vessel without the need to manipulate an intermediary transfer device.

(3) There are many different analyzers in common use. These may have unique sampling vessels. Multiple aliquots must often be prepared from one patient blood specimen into a variety of specialized sample vessels for use in different analyzers. A useful technology would be able to use a wide variety of sample vessels. It would respond to an input signal which identified the analysis required. It would then select and position the appropriate vessel to receive the aliuon(s).

(4) It is often necessary to exclude suspended fibrinous or cellular material, e.g., red blood cells, which may interfere with analyses. A desirable feature of technology for dispensing serum or plasma would be a mechanical filter to remove any suspended particulate material.

(5) The volume transferred may have to be accurately metered, both to conserve the specimen and to provide an optimal amount for a particular analyzer. An automated aliquotter should be able to sense the amount of serum or plasma available and dispense controlled volumes into the various aliquot recipient vessels.

(6) Positive identification of the aliquot, e.g., by label, is necessary since a sample is being transferred from one vessel to another and many other specimens of similar appearance may be handled at the same time. A device for automated accessioning should ensure continuity of identity from the source container (blood collection tube) to each of the aliquots. A preferred means of identity would be a label with a unique identifier which is generated or transferred to the recipient vessel.

(7) Any apparatus which is used to convey sample from a source tube to an aliquot vessel should either be used only once or be thoroughly cleaned between uses. Carry over of less than 1 part per million is desirable and ideally ought to be nil.

(8) Further analyses on any individual or group of specimens may be necessary at a later time, consequently any unused sample is often stored for several days. This must be protected from the effects of evaporation and preserved, usually by refrigeration. The ideal device should prevent evaporation and accidental contamination of the specimen but facilitate removal of further aliquots at a later time.

Conventional sample aliquotting is labor-intensive and has not generally been automated to the same degree as other procedures in clinical laboratories. Automation of sample aliquotting could effectively isolate laboratory personnel from the dangers of blood processing while increasing the speed and efficiency of the overall analytical procedure.

For most analyses of centrifuged blood samples it is necessary to dispense a portion of the sample to alternate containers such as analyzer sample cups. This is done in a number of ways.

In the usual procedure a technologist takes a blood collection tube which has been centrifuged and opens it by removing the stopper from the top. This may create aerosols or splash droplets of infectious serum. Many blood collection tubes are made of glass and the force required to remove the stopper occasionally results in a broken tube. Open or broken tubes increase the risk of sample loss and infectious hazard to the technologist.

A simple disposable transfer pipette is often used to transfer a portion of the serum or plasma. Another popular method of dispensing a sample is to decant an aliquot into the additional recipient containers. If this method is used the blood collection tube must also contain a gel or other barrier such as in U.S. Pat. No. 3,852,194 to Zine to prevent cellular material from being decanted with the serum or plasma. This method is even more hazardous than the first because considerable care and skill is required to decant a small volume of serum or plasma and not to spill any.

Some devices have been made which attempt to address these hazards. One such device is the Tip-Top (TM) Dispenser Cap made by Helena Laboratories of Beaumont Tex. 77704-0752. The Tip Top dispenser is fastened to the open end of a centrifuged blood collection tube, inverted, and then squeezed causing a portion of the sample to be dispensed through an orifice to a sample cup. A disadvantage of the Tip Top dispenser and others like it is that removal of the blood collection tube stopper, a hazardous manual step, is required.

The Pumpette (TM) from Helena Laboratories, Beaumont Tex. 77704-0752 is a disposable, manually operated device which does not require stopper removal to dispense a blood sample from a blood collection tube. However, it delivers only a small stream of serum and its use is slow and cumbersome if large numbers of specimens must be aliquotted quickly.

The CleanTech (TM) system made by CleanTech SCI AG, Langenthal CH-4900, Switzerland consists of several components including a cannula to puncture the stopper, a machine to insert the cannula into the stopper, a pipette to access the sample through the stopper and a pump which fastens to the pipette to draw the sample from the tube. This device goes far to address the hazards of dispensing a sample, but it is a relatively complex device and requires several steps no use.

An important innovation would provide cleaner separation and mechanical filtration of the serum. It is an advantage to detect and avoid aspiration of any fibrous material or to filter it out. Modern analyzers tend to have tiny orifices which are easily clogged by the small clots of fibrin suspended in the serum which may remain or be formed after centrifugation. Some clinical chemistry laboratories filter all serum as a precaution. Filtration may be achieved by a device which is inserted into the open end of the collection tube after centrifugation and permits the one-way flow of serum from the collection tube into a separate sampling container through a filter which prevents fibrin from passing into the serum or plasma sample. Such filtration devices are described, for example, in U.S. Pat. No. 4,464,254 by Dojki and are manufactured and distributed under the name of "serum/plasma filter" by W. Sarstedt, Inc. Other devices have been described by U.S. Pat. No. 3,929,646 by Adler, U.S. Pat. No. 4,602,995 by Cassaday, U.S. Pat. No. 4,487,696 by Ferrara and U.S. Pat. No. 4,142,668 by Lee. However, their use requires additional manipulation of the collection tube, consequent exposure of the user to the blood specimen and risk of contamination of the sample.

A variety of devices have been suggested and used with which sampling is accomplished by means of a cannula inserted through the stopper of a blood collection tube, e.g. Seebaugh WR et al: An automated device for aseptically aspirating serum from blood collection tubes. IEEE Transactions on Biomedical Engineering Vol. BME: 33, No. 6, June 1986, pp 610-616. Such a device may either penetrate the stopper with a large cannula and then insert a smaller one into the serum through the large one (such as on the Paramax (R) Closed Container Sampling (TM) by Baxter, Irvine Calif. 92718; or directly through the stopper as in the Serumax (TM) by Medical Robotics, Inc., Lexington, Ky. 40510. Such systems aspirate part or all of the serum and transfer it to another vessel or directly to the analyzer. A disadvantage of these systems is the need to thoroughly wash all surfaces which contact the serum to prevent analyte carryover from one specimen to another.

Some blood collection tubes have Seen designed to directly incorporate a means to dispense serum, for example U.S. Pat. No. 4,169,060 by Columbus, but these require that all blood specimens be collected in such tubes.

With any cannula which reaches into the serum there is a danger of penetrating or aspirating some of the gel separator material used in some types of blood collection tubes. The Helena Pumpette (TM) has this risk if the operator pushes the fine aspiration tube too far into the tube. The device described by Seebaugh has sensors to detect the gel layer and avoid its penetration by the cannula.

Aliquots of plasma may be prepared from whole blood with a device such as U.S. Pat. No. 4,847,205 by Burtis. However, the aliquots are very small, being centrifugally distributed into capillaries and the blood must be collected by another apparatus such as a syringe or evacuated blood collection tube and then transferred to this device.

Largely automated aliquotting can be performed with devices such as the Tecan Robotic Sample Processor by Tecan AG, 8634 Hombrechitikon, Switzerland. These devices typically have racks or trays which hold the specimen tube and the vessels for which the aliquots are destined. A sample probe or cannula connected to a pump is manipulated automatically to sip and dispense sample. These devices are generally too inflexible to be of use for the primary aliquotting of samples. They are most suitable for the final dispensing, dilution and sample preparation for a particular analysis, with restricted size and shape of sample and aliquot vessels. Similar robotic systems such as described by U.S. Pat. No. 4,927,545 by Roginski are more flexible in their ability to be adapted to a variety of vessels but require complex programming and use up a great deal of space.

The recipient aliquot containers or sample cups must then be labelled to match the source tube. After one or more aliquots have been dispensed the source tube is usually capped to prevent spillage and evaporation and stored for several days. Occasionally this tube is recovered from storage and more serum or plasma is removed for further testing. The additional cap is an added expense, whereas if the original stopper is used there is increased contact with the hazardous biological fluid.

SUMMARY OF THE INVENTION

The present invention relates to an apparatus and method for dispensing a liquid such as blood, blood sera, or blood plasma from a blood collection tube which is closed with a stopper.

The invention pertains to a disposable apparatus which has a stopper piercing element that reaches into the interior of a blood collection tube through the tube's stopper. The piercing element is just long enough to allow a fluid passage contained within the piercing element to reach inside the tube, but no longer. The apparatus also includes a gas passage which provides a means to force an amount of gas into the blood collection tube thereby forcing an amount of fluid out of the tube through a fluid passage within the apparatus. The gas passage is made small enough so that when the fluid-containing tube is inverted, the liquid contained therein is restrained from entering the gas passage under the influence of gravity. The apparatus also provides a means for guiding gas into a tube through the gas passage by providing a sealing means between the apparatus and the stopper of a blood collection tube. The apparatus has a fluid path to provide a channel for liquid to be dispensed from an inverted blood collection tube into a number of subcontainers.

Also described is a liquid sensing means for generating a signal representative of the amount of liquid contained within a blood collection tube, a data input means for indicating the amount of liquid to be dispensed from a blood collection tube, and a control means to regulate the introduction of a gas into a blood collection tube according to signals provided by the data input means and the liquid sensing means.

The method of the invention involves inserting a disposable apparatus through the stopper of a liquid-containing blood collection tube; making and maintaining a gas-tight seal between the apparatus and the stopper of said tube; inverting the blood collection tube; forcing a predetermined amount of gas through the apparatus into the blood collection tube; and receiving from the apparatus a quantity of liquid proportional to the amount of gas that was forced into said tube.

Also described is a method whereby signals are received from a liquid sensing means (representative of the amount of liquid contained within a blood collection tube) and a data input means (representative of the amount of liquid to be dispensed from a blood collection tube) by a control means in order to regulate the introduction of a gas into a blood collection tube for the purpose of dispensing a portion of the liquid contained within a blood collection tube.

BRIEF DESCRIPTION OF THE DRAWINGS

FIG. 1a shows the automated aliquotter module indicating the position of the analyzer tray containing analyzer cups.

FIG. 1b shows another view of the automated aliquotter module illustrating the input and output trays for blood collection tubes.

FIG. 2a shows the disposable pipetter which is used within the automated aliquotter module, or a manually operated embodiment of the aliquotter, to facilitate dispensing of serum/plasma from a closed blood collection tube.

FIG. 2b shows a disposable pipetter used with a centrifuged blood collection tube.

FIG. 3a shows an automated aliquotter module inserting a disposable pipetter into the stopper of a closed blood tube.

FIG. 3b shows a disposable pipetter having been inserted through the slopper of a closed blood tube.

FIG. 3c, the automated aliquotter module having inverted a tube is dispensing fluid through a disposable pipetter into an analyzer cup.

FIG. 3d shows a blood tube which has had a portion of its contents dispensed being ejected from the automated aliquotting module.

DESCRIPTION OF SPECIFIC EMBODIMENTS

Figure 4:
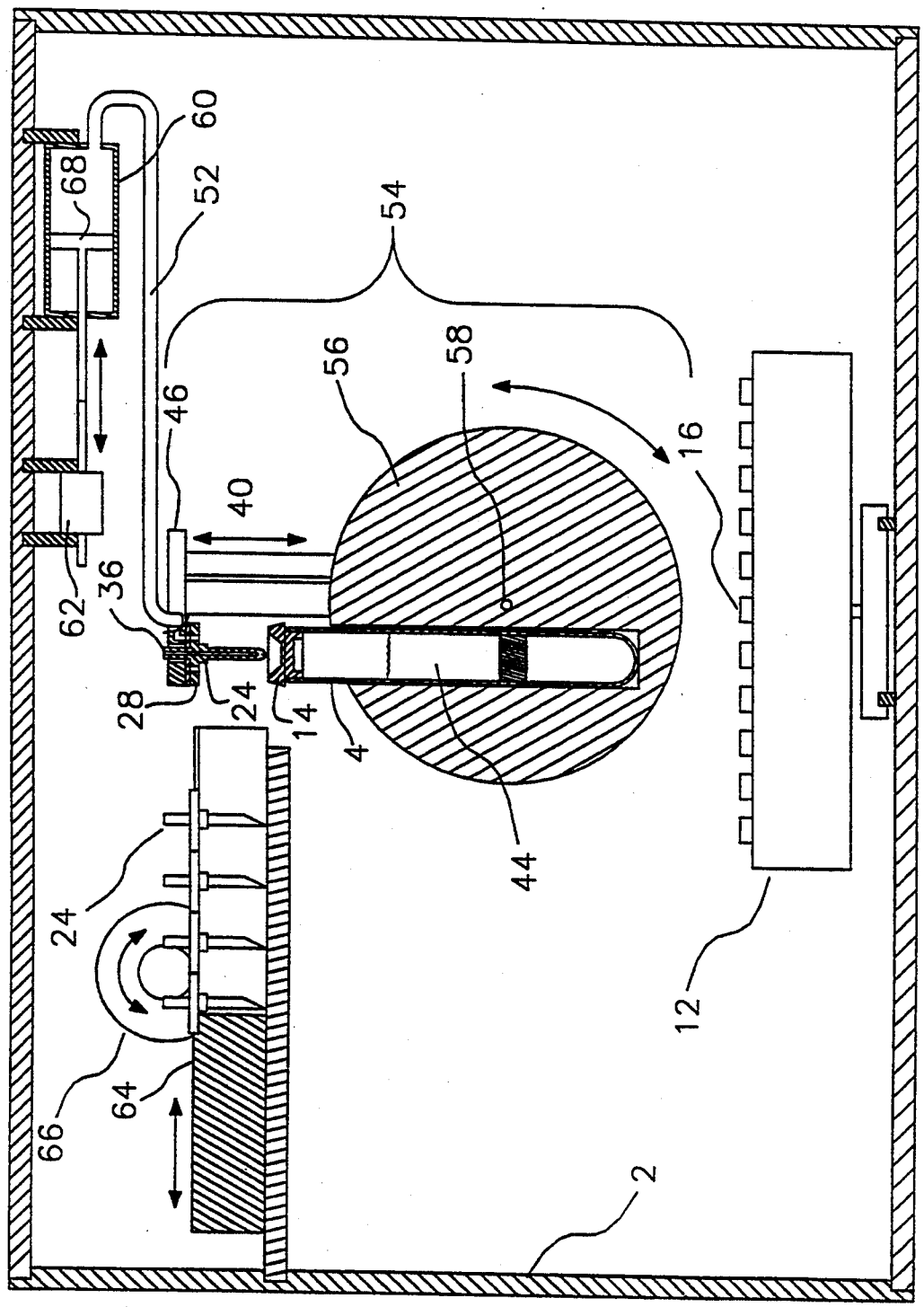
FIG. 4, shows the mechanisms used to manipulate a sample tube within the aliquotter module and to facilitate dispensing of fluid from a sample tube illustrating the operation of the automated aliquotter.

The present invention is an apparatus for dispensing a specimen of liquid from a closed container and directing the liquid into one or more subcontainers. More specifically, the present invention is an apparatus for dispensing blood, blood sera or blood plasma from a blood collection tube into analyzer sample cups to be used within automated blood analyzers. In the following description the disposable component of the invention is termed "disposable pipetter" and the machine component is termed "aliquotter module".

FIG. 1A shows one view of the preferred embodiment of the present invention showing the general form of the machine component as it would appear in use. An analyzer tray 12 is shown positioned in output bay 18 of the aliquotter module 2. The analyzer tray 12 holds a multiplicity of small analyzer cups 16 which receive a portion of liquid from a blood collection tube being processed within aliquotter module 2. When a number of analyzer cups have received a liquid portion, the analyzer tray 12 is manually removed from the aliquotter module 2 and placed into an automated analyzer, such as are common in many clinical laboratories, where the dispensed portions are analyzed. FIG. 1b shows another view of the aliquotter module 2 better showing the input tray 8 and output tray 10. Input tray 8 receives one or more blood tubes 4 which are individually received and processed by aliquotter module 2. Output tray 10 receives blood tubes 4 one by one from aliquotter module 2 after a portion of each one's contents have been dispensed. The tubes in output tray 10 are periodically removed by hand to be stored for later reference or are disposed of.

Again referring to FIGS. 1a and 1b, aliquotter module 2 receives a liquid-containing blood tube in input tray 8, accepts the blood tube from the input tray, identifies the blood tube using a barcode reader, measures the quantity of liquid within the blood tube, dispenses the liquid contained within the tube into one or more analyzer cups 16 which are located in analyzer tray 12, and then ejects the processed blood tube into output tray 10. The amount of liquid to be dispensed in each dispensing operation is predetermined on the basis of information about the sample such as analyte volume, sample quality, test requisitions and test priority. Aliquotter module 2, having dispensed from a blood tube a predetermined amount of liquid into one or more analyzer cups 16, then ejects the blood tube from the aliquotter into output tray 10. Analyzer tray 12 may then be removed from the apparatus by the operator to be taken to the appropriate analyzer for analysis of the liquid contained in the analyzer cups.

Still referring to FIG. 1b, the preferred embodiment of aliquotter module 2 has a keyboard 20 for data input and a display screen 22 to relay important information to an operator. The keyboard 20 allows a user to control the parameters of the machine and to input information regarding a blood sample that is being aliquotted by the apparatus. The display screen 22 provides a confirmation of what has been typed on the keyboard as well as supplying error messages and information about said blood sample. The keyboard and display portions of the apparatus are of a type found on many electronic devices.

FIG. 2a shows disposable pipetter 24 which is used within the aliquotter module 2 of FIGS. 1a and 1b or within a manually operated aliquotting device (depicted in FIG. 6) to dispense a portion of liquid from a closed, liquid-containing blood collection tube. Disposable pipetter 24 is preferably injection molded in one piece of polystyrene or other substantially hard plastic. Disposable pipetter 24 is fashioned so as allow liquid to be expressed from a blood tube 4 by providing for a gas such as air to be forced into the tube (pressurizing the interior of the tube) causing liquid to be expressed from the tube through serum conduit 30. The disposable pipetter comprises a stopper spike 26, base plate 28, serum conduit 30, air inputs 32, air groove 34, and serum spout 36. Air groove 34 is made small enough to allow the passage of pressurized gas into the tube, but to resist the flow of fluid out of the blood tube.

FIG. 2b shows the disposable pipetter 24 as it appears in use. The stopper spike 26 punctures tube stopper 14 and the pipetter 24 is pushed onto the tube stopper until the base plate 28 is comes to rest against the stopper rim 40. The disposable pipetter 24 is held against the stopper (by a mechanism depicted in FIGS. 3 and 4) causing plate 28 to seat against the stopper rim 40 thereby making air-tight seal 39 where stopper rim 40 engages base plate 28. Once disposable pipetter 24 has been thus positioned, the tube is inverted and liquid 44 contained in blood tube 4 rests in the stopper end of the tube above the stopper spike 26 of the disposable pipetter 24 as shown. With the blood tube in the inverted position, the volume of the liquid contained therein may be measured optically. If the tube were not inverted it would be more difficult to measure the volume of blood serum or plasma contained therein because the unknown volume of cellular matter in the bottom of the tube affects the surface level of the liquid portion. With the tube inverted the volume of liquid is always measured from the datum of the stopper. The volume of liquid is then measured by liquid level sensor 41. A metered amount of air is then forced through the air inputs 32, into the airgap 42, and further through air groove 34 pressurizing the interior of the blood tube 4. As the blood tube 4 is pressurized, liquid 44 is forced through the serum conduit 30 thereby dispensing it from tube 4 into analyzer cup 16. Stopper spike 26 is made just long enough so that serum conduit 30 reaches just inside of the blood tube with an opening positioned proximal to the interior surface of the tube stopper 14 so that when liquid is being dispensed, virtually all the liquid within the tube is accessible. If the stopper spike 26 was too long there would be a certain volume of liquid which could not be accessed by the method of this invention because there would be some liquid positioned between the opening of the liquid path and the interior surface of the stopper. Therefore the length of the stopper spike 26 is made just long enough to reach just inside the thickest stoppers that are to be processed. When processing tubes with thinner stoppers there would be a small amount of inaccessible liquid.

Again refering to FIG. 2b, liquid level sensor 41 consists of a group of light emitting diodes 43 interleaved with optical sensors 47 which utilize optical fibers 37a and 37b to position the sensors and light sources in a fine linear array within level sensor 41. The light from light emitting diode 43 shines through optical fiber 37a into the interior of tube 4 illuminating the contents of the tube. Optical sensor 47 receives reflected light through optical fiber 37b indicative of the contents of the tube nearest to that fiber. An optical fiber that is located near a portion of the tube that has air just on the other side of the tube wall receives a different amount of light than an optical fiber that is positioned at a portion of the tube that has liquid just on the other side of the tube wall. In this way, knowing the position of the optical fibers which show an air/liquid interface and knowing the position of the interior surface of stopper 14 it is possible to calculate the volume of liquid 44 contained within tube 4. The volume of available liquid is an important piece of information for aliquotting blood serum or plasma for analysis because if there is not enough serum or plasma to accomplish all of the desired tests, the automated aliquotter (or an operator) must make decisions about how to best dispense the liquid to accomplish the most important tests.

FIGS. 3a to 3d illustrate the steps required to aliquot a sample according to the method of the present invention.

FIG. 3a shows the first step of inserting a disposable pipetter 24 into the stopper of a separated blood tube 4. Blood tube 4, as depicted here, is of the type commonly used for blood collection and separation in the clinical laboratory and is of the type that has a physical barrier 45 like that found in the SST Vacutainer ™ made by Becton-Dickinson of East Rutherford, N.J. Disposable pipetter 24 is shown held in pipetter holder 46. Pipetter holder 46 includes inner seal 48, outer seal 50, and air supply 52. Pipetter holder 46 and blood tube 4 are brought together under sufficient force Eo cause disposable pipetter 24 to puncture through tube stopper 14 and for base plate 28 to come to rest against stopper rim 40.

FIG. 3b shows the disposable pipetter 24 in its rest position after insertion into the tube stopper 14.

After the disposable pipetter 24 is inserted into the stopper 14 the integrated assembly 54 comprising the blood tube 4, pipetter holder 46, and the disposable pipetter 24 is inverted as shown in FIG. 3c. Once the integrated assembly 54 has been inverted, the liquid 44 comes to rest above stopper 14 and disposable pipetter 24 in the position shown. The volume of liquid available is then measured by liquid level sensor 41. An analyzer cup 16 is positioned beneath the serum spout 36 in preparation to receive liquid such as serum or plasma from serum spout 36. A controlled amount of air is then forced through air supply 52, though air inputs 32 into airgap 42 and further through air groove 34 thus pressurizing the interior of blood tube 4. Pressurizing the interior of blood tube 4 forces some of liquid 44 to pass through serum conduit 30 dispensing it from serum spout 36 into analyzer cup 16. More than one analyzer cup 16 may be used for a single blood tube by dispensing liquid 44 in successive dispensing operations. Inner seal 48 and outer seal 50 seal against disposable pipetter 24 so as to confine gas to pass from air supply 52 through air inputs 32.

After a specific amount of serum or plasma has been dispensed from the tube into one or more sample cups pipetter holder 46 moves away from blood tube 4 and the blood tube together with the disposable pipetter 24 is released from pipetter holder 46 and is either stored for later testing or is disposed of. FIG. 3d illustrates this release action. Although this phase of the operation is shown with the tube in a vertical orientation, it is not necessary that it be so.

FIG. 4 illustrates the automated aliquotter module in a simplified form showing important mechanical elements of the apparatus. Blood tube 4 is shown in tube cradle 56 which rotates about axle 58 in preparation for dispensing fluid according to the method depicted in FIGS. 3a to 3d. Pipetter holder 46 is located on tube cradle 56 and moves as shown under the influence of an electric motor in order to push pipetter 24 through stopper 14 and to hold pipetter 24 and tube 4 in place when cradle 56 is rotated. The movement of pipetter holder 46 and other machine motions may be achieved by other means such as pneumatic, hydraulic, or even manual means and therefore the use of an electric motor does not constitute a limitation of the present invention. Also shown is gas cylinder 60 which is actuated by linear drive motor 62 to supply a metered amount of gas to be injected into tube 4 causing fluid to be dispensed according to the method of the invention. Pipetter carriage 64 supplies disposable pipetters 24 to pipetter holder 46 in an automated fashion so that the apparatus may process a number of blood tubes one at a time each one using a pipetter. Carriage motor 66 moves disposable pipetters 24 into a position accessible to pipetter holder 46. Also shown is analyzer tray 12 holding a number of analyzer cups 16. Analyzer tray is rotated about a central axis in order to position an analyzer cup 16 beneath serum spout 36 of a tube that has been inverted by cradle 56 and that is to have its contents dispensed.

In use, the apparatus depicted in FIG. 4 functions in the following way. Pipetters 24 are loaded into pipetter carriage 64 by an automated handler (not shown) or by hand in preparation for the operation of aliquotter module 2. Blood tube 4, which is to have its contents dispensed into analyzer cups 16, is loaded into tube cradle 56 in an automated fashion depicted in FIG. 5a or by hand. Pipetter holder 46 receives a disposable pipetter 24 from pipetter carriage 64. When blood tube 4 has been positioned in tube cradle 56 and pipetter holder 46 has positioned disposable pipetter 24 as shown, pipetter holder 46 moves disposable pipetter 24 so that it punctures stopper 14 of blood tube 4 and continues to supply a force to hold the tube within cradle 56 and to cause base plate 28 to seal against stopper rim 40. Integrated assembly 54 is then inverted so that serum spout 36 is positioned above an analyzer cup 16. With the assembly inverted, it is possible to optically determine the volume of dispensible liquid within the blood tube for purposes of making decisions regarding how the sample should be divided between subcontainers. Once inverted, linear drive motor 62 under automated control or manual control, moves piston 68 so that air is forced through air supply 52, through the disposable pipetter, and into the inverted blood tube. As air is forced into blood tube 4 the liquid contained therein is displaced through serum conduit 30 and into an analyzer cup 16. If additional analyzer cups need to be filled, linear drive motor 62 stops (thereby preventing further liquid to be dispensed from the blood tube) and analyzer tray 12 is rotated so that a different analyzer cup is positioned beneath serum spout 36. When a new analyzer cup is positioned beneath the serum spout, linear drive motor 62 is again engaged causing more of liquid 44 to be dispensed according to the procedure outlined above. This procedure may be repeated to fill several sample cups. When a sufficient amount of liquid 44 is dispensed from blood tube 4 then blood tube 4 and disposable pipetter 24 are removed together from the apparatus by manual or automated handling means. The resulting blood tube/pipetter assembly is then stored for later use or is disposed of.

FIGS. 5a to 5h illustrate further the operation of the automated aliquotter module. FIGS. 5a–5d show front views beneath corresponding side views (FIGS. 5e–5h) of tube cradle 56, blood tube 4, and pipetter holder 46.

Figure 5:
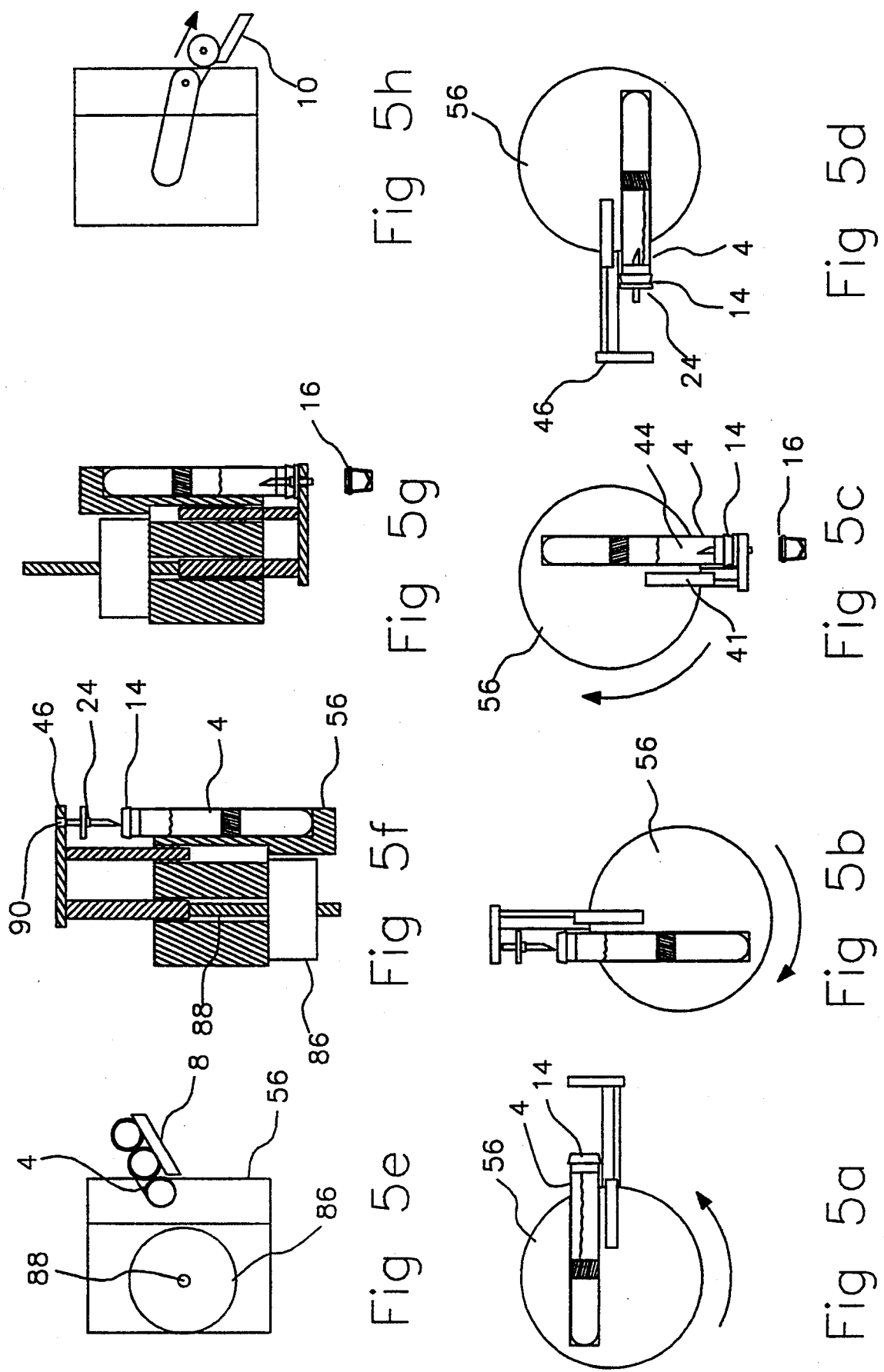
FIGS. 5a and 5e show tubes in an input region and how the automated aliquotter module receives a single tube to be aliquotted.
FIGS. 5b and 5f show the automated aliquotter positioning a blood tube in an upright position to receive a disposable pipetter.
FIGS. 5c and 5g show the aliquotter inverting a blood tube in order to dispense a portion of the liquid contained within it into an analyzer cup.
FIGS. 5d and 5h show the aliquotter ejecting a tube that has been aliquotted.

Referring to FIGS. 5a and 5e, blood tube 4 is loaded into tube cradle 56 by gravity from input tray 8. In this way a single blood tube is loaded in preparation for dispensing the contents of the tube. Tube cradle 56 then rotates until it is in the position indicated by FIGS. 5b and 5f. In FIGS. 5b and 5f pipetter holder 46 is shown as it is about to insert disposable pipetter 24 into stopper 14 of tube 4. Once pipetter 24 has been positioned by pipetter carriage 64 of FIG. 4 as shown, clamping motor 86 turns lead screw 88 causing pipetter holder 46 to move towards blood tube 4. Pipetter holder 46 is stopped momentarily when it has grasped disposable pipetter 24 so as to allow pipetter carriage 64 (FIG. 4) to move out of the way. Pipetter holder 46 grabs hold of pipetter 24 by means of a tight-fitting hole 90. Pipetter holder 46 then continues to move toward blood tube 4 until pipetter 24 is pierced through tube stopper 14 and is clamped against said stopper. Once disposable pipetter 24 is fully inserted into stopper 14 and is clamped, tube cradle 56 rotates so as to position blood tube 4 and disposable pipetter 24 as shown in FIGS. 5c and 5g. When the position shown in FIG. 5c is achieved, the volume of available liquid can be measured by liquid level sensor 41. A controlling computer (or the operator) then uses the volume information together with information regarding sample cup type, test requisitions, sample quality, and test priority to determine the most optimal division of the liquid among a number of sample cups. Liquid 44 is then dispensed in amounts corresponding to signals provided by the operator or the controlling computer. Once a desired amount of liquid has been dispensed into one or more subcontainers, tube cradle 56 is rotated further into the position illustrated by FIGS. 5d and 5h. FIGS. 5d and 5h show how a blood tube that has been aliquotted is unloaded from the aliquotter. Once tube cradle 56 has been rotated to the position shown, pipetter holder 46 is moved away from blood tube 4 leaving disposable pipetter 24 in tube stopper 14. Blood tube 4 with disposable pipetter 24 then moves into output tray 10 under the influence of gravity. Tubes that are found in output tray 10 are later removed manually for storage or disposal.

Figure 6:
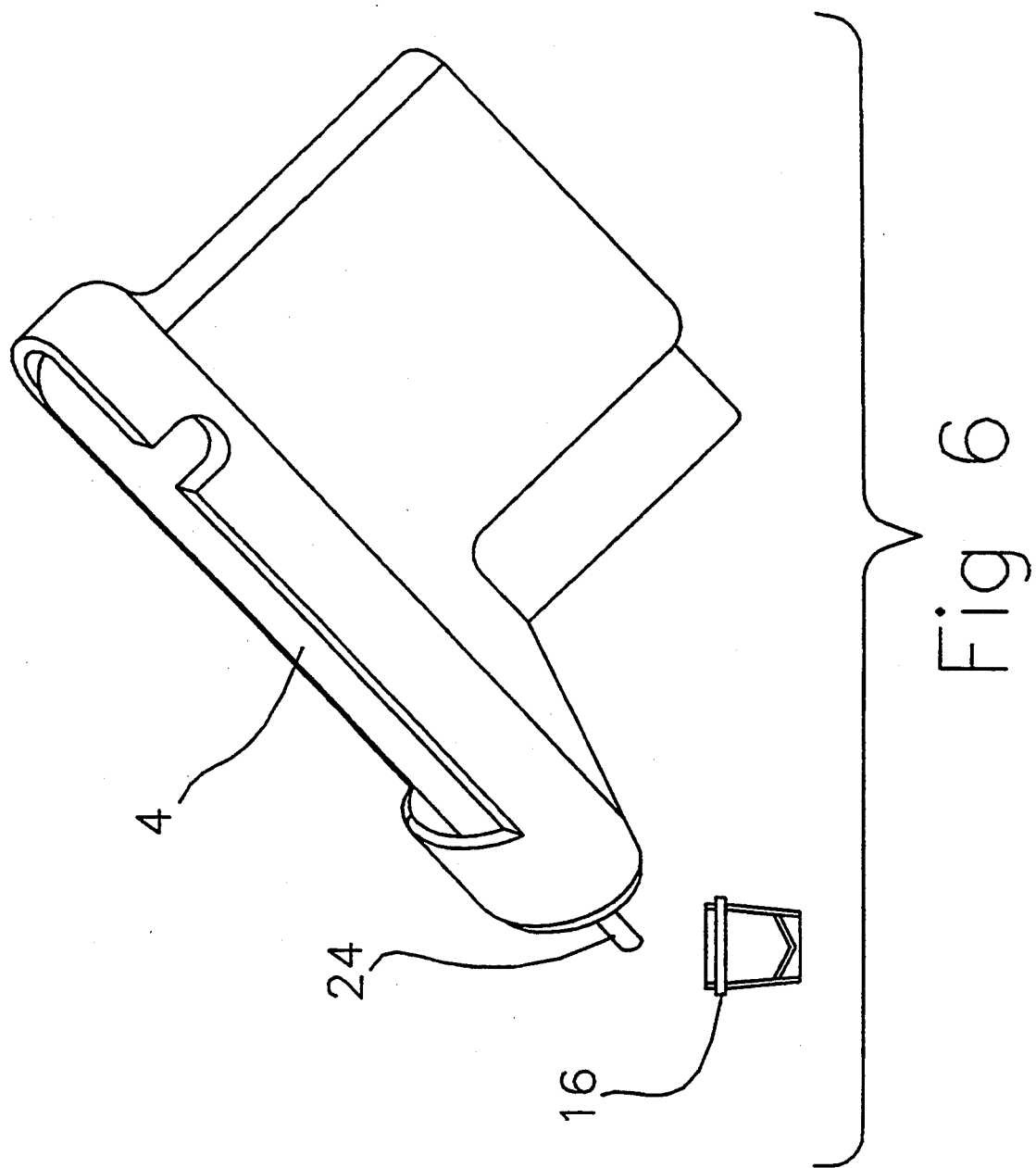
FIG. 6 shows a hand-operated implementation of the aliquotter module for use in a non-automated environment.

An alternate embodiment of the present invention is shown in FIG. 6. Although this implementation is a manually operated one, it still functions following the method of the present invention. Disposable pipetter 24 is inserted onto blood tube 4, the tube is then inverted and a gas such as air is injected into tube 4 causing liquid 44 to be dispensed from disposable pipetter 24 into analyzer cup 16. Insertion of disposable pipetter 24 into the stopper of blood tube 4 may be accomplished manually. If this alternate embodiment is used to re-aliquot a sample which was previously had a portion of its contents dispensed by an automated aliquotter (shown in FIG. 1), a disposable pipetter will have already been inserted into the stopper of blood tube 4 and it may be used again.

Figure 7:
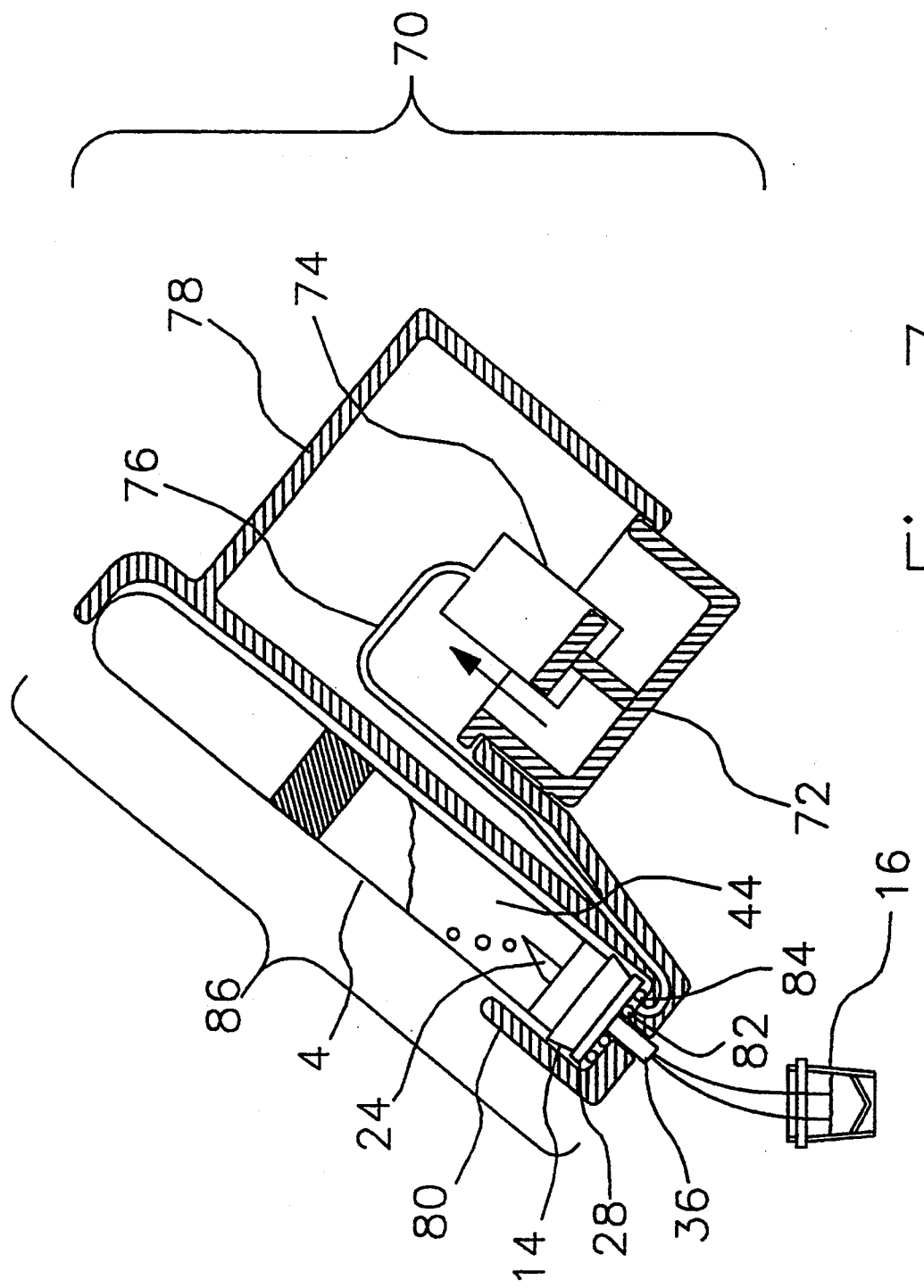
FIG. 7 shows a cross-sectional view of the hand-operated aliquotter indicating how its functions are accomplished.

FIG. 7 shows a cross-sectional view of the alternative embodiment of the aliquotter module. Components of the manual aliquotter module 70 include trigger 72, air pump 74, air line 76, handle 78, tube holder 80, inside seal 82 and outside seal 84. Also shown are the blood tube 4, disposable pipetter 24 and analyzer cup 16.

In use, disposable pipetter 24 may be manually inserted through stopper 14 of blood tube 4 in preparation for dispensing a portion of the liquid contained in blood tube 4 into an analyzer cup 16. Assembly 86 resulting from the union of blood tube 4 and pipetter 24 is then loaded into manual aliquotter module 70 by inserting the pipetter end of assembly 86 in the end of tube holder 80 which contains inside seal 82 and then forcing assembly 86 into the position illustrated in the figure. As assembly 86 is being thus positioned within manual aliquotter module 70, inside seal 82 and outside seal 84 press against base plate 28 of disposable pippetter 24 to create a confined path for air to be forced from air pump 74 through pipetter 24 into tube 4 thereby causing liquid 44 to be dispensed from assembly 86 into analyzer cup 16. Once assembly 86 has been positioned and said seals have been established then manual aliquotter module 70 is positioned so that liquid 44 is positioned substantially above stopper 14 as shown. Trigger 72 is then depressed in the direction indicated by the arrow causing air pump 74 to displace air through air line 76, between inside seal 82 and outside seal 84, and further through disposable pipetter 24 into blood tube 4. As this air is displaced into tube 4, liquid 44 is then forced out of serum spout 36 into analyzer cup 16. In this way liquid can be easily and safely dispensed from a closed blood collection tube using the apparatus and method of the present invention.

Figure 8:
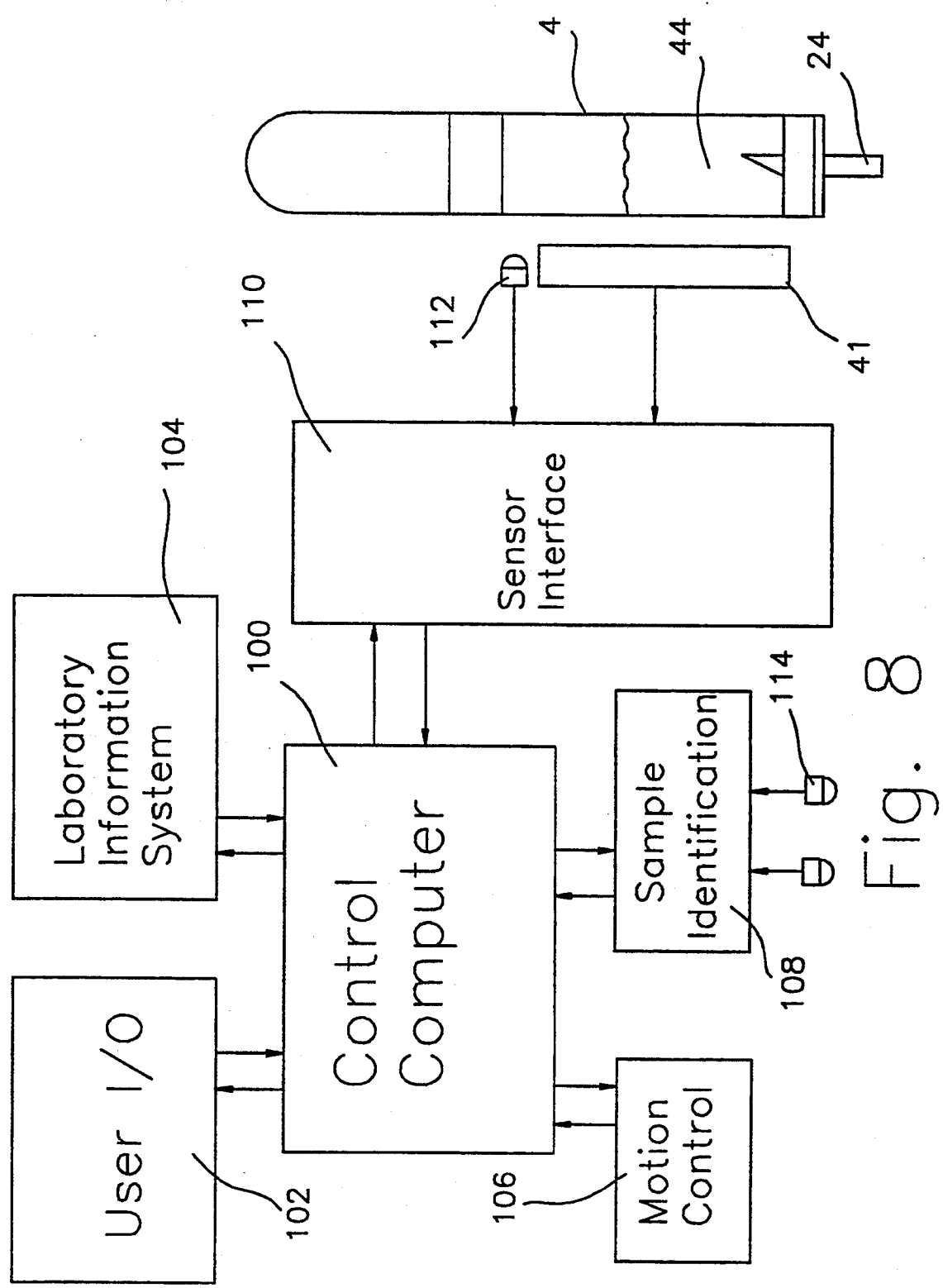
FIG. 8 shows the process control system for the automated aliquotter.

FIG. 8 shows the process control system for the automated aliquotter in block diagram form. Control computer 100 controls the automated aliquotter utilizing user supplied information, sensor-derived information, and laboratory database information. User supplied information enters via user I/O pore 102 which, in the preferred embodiment, includes an alpha-numeric keypad. Control computer 100 also relays process and control information to the user through the user I/O port 102. Information regarding sample identification and patient information contained within the laboratory database is relayed to and from control computer 100 through laboratory information system 104. Laboratory information system 104 is of a type typical in many large laboratories. Motion control module 106 drives the various mechanical motions of the aliquoter by powering motors according to signals provided by control computer 100. Said motors include linear drive motor 62 of FIG. 4 receiving said signals for dispensing a predetermined volume of sample liquid 44. Position and other information about the status of the motion systems is fed back to control computer 100 through motion control module 106. Sample identification module 108 allows barcode readers 114 to be interfaced with control computer 100 for the purpose of identifying blood tubes and sample cups. This is an important aspect of the control system because sample identification links the blood sample to information required to determine which test requisitions are to be performed on the present sample and how the sample is to be divided. Sensor interface 110 receives signals from various sensors and converts these signals into a form which can be used by control computer 100. These sensors include serum quality sensor 112 and liquid level sensor 114 as well as various process and status sensors. Serum quality sensor 112 and liquid level sensor 41 provide information to control computer 100 for making decisions about how to divide a sample among several sample cups for performing various tests. There may be more than one serum quality sensor 112 and each one may be configured to provide an indication of a different sample parameter.

We claim:

1. Apparatus for dispensing a liquid such as blood, blood sera or blood plasma from a closed blood collection tube, comprising:
   (a) closure piercing means having an end shaped for piercing a stopper of a blood collection tube and for extending into the tube;
   (b) liquid path means located within said closure piercing means for defining an opening through the stopper when the closure piercing means is inserted through the stopper of the blood collection tube;
   (c) gas passage means to allow gas to be introduced into the interior of the blood collection tube for the purpose of dispensing liquid from the tube;
   (d) gas connection means for making a substantially leakproof connection between the gas passage means and a gas source;
   (e) input means to produce a first signal indicative of a specified quantity of liquid to be dispensed; and
   (f) controlling means responsive to the first signal to regulate the introduction of gas into the blood collection tube so that the specified quantity of liquid is dispensed.

2. The apparatus of claim 1 further including a sensing means to determine the amount of liquid contained within the blood collection tube and to produce a second signal indicative of that amount, wherein the controlling means is responsive to the first and second signals to regulate the introduction of gas into the blood collection tube so that the specified quantity of liquid is dispensed.

3. The apparatus of claim 1 further including
   sensing means to determine the amount of liquid dispensed and to produce a dispense signal indicative of the amount of liquid dispensed; and
   comparison means to compare the first signal and the dispense signal and to indicate if the amount of liquid dispensed was less than the specified quantity of liquid to be dispensed.

4. Apparatus for dispensing a liquid such as blood, blood sera or blood plasma from a closed blood collection tube, comprising:
   (a) closure piercing means having an end shaped for piercing a stopper of a blood collection tube and for extending into the tube so that the end is immersed in the liquid;
   (b) liquid path means located within said closure piercing means for defining a conduit through the stopper and into the liquid when the closure piercing means is inserted through the stopper of the blood collection tube and into the liquid;
   (c) gas passage means to allow gas to be introduced into the interior of the blood collection tube for the purpose of dispensing liquid from the tube;
   (d) gas connection means for making a substantially leakproof connection between the gas passage means and a gas source;
   (e) input means to produce a first signal indicative of a specified quantity of liquid to be dispensed; and
   (f) controlling means responsive to the first signal to regulate the introduction of gas into the blood collection tube so that the specified quantity of liquid is dispensed.

5. Apparatus for dispensing a liquid such as blood, blood sera or blood plasma from a blood collection tube closed at one end by a stopper and inverted so that the liquid is contained in the tube above the stopper, comprising;
 (a) closure piercing means having an end shaped for piercing a stopper of a blood collection tube and for extending into the tube;
 (b) liquid path means located within said closure piercing means for defining an opening through the stopper when the closure piercing means is inserted through the stopper of the blood collection tube;
 (c) gas passage means to allow gas to be introduced into the interior of the blood collection tube for the purpose of dispensing liquid from the tube;
 (d) gas connection means for making a substantially leakproof connection between the gas passage means and a gas source;
 (e) input means to produce a first signal indicative of a specified quantity of liquid to be dispensed; and
 (f) controlling means responsive to the first signal to regulate the introduction of gas into the blood collection tube so that the specified quantity of liquid is dispensed.

6. Method of dispensing a liquid such as blood, blood sera, or blood plasma from a blood collection tube closed at one end by a stopper and inverted so that the liquid is contained in the tube above the stopper, comprising the steps of:
 (a) inserting dispensing apparatus through the stopper of a closed blood collection tube which contains a liquid;
 (b) making and maintaining a seal between the dispensing apparatus and the stopper of the blood collection tube;
 (c) forcing through a first passage in the dispensing apparatus a quantity of gas into the tube to displace a predetermined amount of liquid from the tube through the dispensing apparatus; and
 (d) receiving through a second passage in the dispensing apparatus the displaced amount of liquid.

7. Method of claim 6 wherein the receiving step is preceded by inverting the blood collection tube so that liquid contained in the tube is above the stopper.

8. The method of claim 7 wherein the introducing and displacing step includes:
 (a) determining the amount of liquid in the blood collection tube and producing a first signal indicative of that amount
 (b) producing a second signal indicative of the amount of sample to be displaced; and
 (c) regulating in response to the first and second signals the introduction of the gas into the blood collection tube so that the predetermined amount of liquid is dispensed.

9. The method of claim 6 further including the step of disconnecting the gas supply from the dispensing apparatus after the receiving step.

10. The method of claim 9 further including the step of leaving the dispensing apparatus inserted into the blood collection tube after the gas supply is disconnected.

11. Apparatus for dispensing a predetermined volume of liquid from a closed blood collection tube comprising:
 (a) a closed blood collection tube containing a liquid;
 (b) dual conduit means connected to the tube and having a first conduit providing a passageway for gas to be introduced into the tube and a second conduit inserted into the closed tube and providing a passageway for liquid to be displaced from the blood collection tube into a receiving vessel;
 (c) connection means for connecting a gas supply to the first conduit of the dual conduit means and for disconnecting the gas supply from the first conduit of the dual conduit means;
 (d) displacement means, responsive to a dispensing signal, for introducing a volume of gas through the first conduit of the dual conduit means into the blood collection tube, whereby a predetermined volume of liquid is dispensed from the blood collection tube through the second conduit of the dual conduit means; and
 (e) controlling means for receiving a signal indicative of the predetermined volume of liquid to be dispensed from the blood collection tube, and generating a dispensing signal to dispense the predetermined volume of liquid from the blood collection tube.

12. Apparatus for dispensing a predetermined volume of liquid from a blood collection tube closed at one end by a stopper and positioned in an inverted orientation so that the liquid is contained in the tube above the stopper, comprising:
 (a) dual conduit means having a first conduit providing a passageway for gas to be introduced into a blood collection tube containing a liquid and a second conduit providing a passageway for liquid to be displaced from the blood collection tube into a receiving vessel;
 (b) insertion means responsive to an insertion signal for inserting the dual conduit means into the blood collection tube;
 (c) connection means for connecting a gas supply to the first conduit of the dual conduit means and, after a predetermined volume of liquid has been dispensed from the blood collection tube, disconnecting the gas supply from the first conduit of the dual conduit means;
 (d) displacement means, responsive to a dispensing signal, for introducing a volume of gas through the first conduit of the dual conduit means into the blood collection tube, whereby a predetermined volume of liquid is dispensed from the blood collection tube through the second conduit of the dual conduit means; and
 (e) controlling means for generating the insertion signal to control the insertion of the dual conduit means into the blood collection tube, and further for receiving a signal indicative of the predetermined volume of liquid to be dispensed from the blood collection tube, and generating a dispensing signal to dispense the predetermined volume of liquid from the blood collection tube.

13. Method for dispensing a volume of liquid from a blood collection tube that contains liquid and is closed at one end by a stopper, comprising the steps of:
 (a) providing a conduit member having opposite ends and a gas passageway and a liquid passageway extending through the conduit member;
 (b) orienting the conduit member and tube so that one end of the conduit member extends through the stopper and so that the contained liquid is above the stopper;

(c) connecting the gas passageway to a gas supply for introducing gas into the blood collection tube through the gas passageway;

(d) responding to a dispense signal by introducing a volume of gas into the blood collection tube through the gas passageway thereby dispensing a selected volume of liquid out of the blood collection tube through the liquid passageway; and (e) after the selected volume of liquid has been dispensed, disconnecting the gas passageway from the gas supply leaving the dual conduit means with the blood collection tube.

* * * * *